United States Patent [19]
Pigneul

[11] Patent Number: 4,731,071
[45] Date of Patent: Mar. 15, 1988

[54] LIQUID-ABSORBENT DISPOSABLE ARTICLE

[75] Inventor: Raymond Pigneul, Durrenentzen, France

[73] Assignee: Beghin-Say S.A., Thumeries, France

[21] Appl. No.: 756,976

[22] PCT Filed: Nov. 6, 1984

[86] PCT No.: PCT/FR84/00248

§ 371 Date: Jul. 8, 1985

§ 102(e) Date: Jul. 8, 1985

[87] PCT Pub. No.: WO85/02110

PCT Pub. Date: May 23, 1985

[30] Foreign Application Priority Data

Nov. 8, 1983 [FR] France ................ 83 17723

[51] Int. Cl.$^4$ ............................................. A61F 13/16
[52] U.S. Cl. .................................. 604/385 R; 604/368
[58] Field of Search ................ 604/385, 364, 368, 370

[56] References Cited

U.S. PATENT DOCUMENTS

| | | | |
|---|---|---|---|
| 3,636,952 | 1/1972 | George | 604/364 |
| 3,670,731 | 6/1922 | Harmon | 604/364 |
| 3,731,688 | 5/1973 | Litt | 604/378 |
| 3,814,100 | 6/1979 | Nystrand | 604/385 R |
| 3,874,385 | 4/1975 | Gellert | 604/370 |
| 3,916,900 | 11/1975 | Breyer et al. | 604/370 |
| 3,968,798 | 6/1976 | Hokanson | 604/370 |
| 4,041,950 | 8/1977 | Jones | 604/385 R |
| 4,230,113 | 10/1980 | Mehta | 604/385.1 |
| 4,317,449 | 3/1982 | Nowakoski | 604/368 |
| 4,560,380 | 12/1985 | Tharel | 604/385.1 |
| 4,576,596 | 3/1986 | Talleson et al. | 604/370 |

*Primary Examiner*—John D. Yasko
*Attorney, Agent, or Firm*—A. W. Breiner

[57] ABSTRACT

The invention relates to the sanitary field and more particularly to a disposable article which absorbs liquids and comprises an absorbent mattress (2) having a rectangular shape and covered on its inner face with a liquid permeable sheet (9) such as a non-woven sheet and on its outer face with a liquid impervious sheet (8) such a polyethylene sheet, both sheets being joined together along their edges, said mattress (2) being formed by three superposed layers (14a, 14b, 14c) of cellulose foam sheet, the outer layer being continuous while the other layers (14b, 14c) are comprised of two adjacent semi-layers and arranged symmetrically with respect to the longitudinal axis of the mattress. The mattress is also provided with lateral mono-layer extensions (16). Application to the making of disposable napkins for babies or adults, sanitary towels, dressings.

6 Claims, 12 Drawing Figures

LIQUID-ABSORBENT DISPOSABLE ARTICLE

The invention has as its subject a liquid-absorbent disposable article. This article is intended for use as a complete diaper change for adults or babies, but it can also be used as a menstrual napkin for absorbing the menstrual liquid, or as a dressing.

In addition to the function of absorbing liquids, such an article should avoid keeping the liquid in contact with the user's skin in order, on the one hand, to improve the general comfort of the user and, more especially, as far as possible, to prevent the liquid, which undergoes a degradation phenomenon known as maceration, causing skin irritation. For this purpose, it is necessary that the fluid migrates to regions of the padding removed from the user's skin.

There has thus been proposed in French Pat. Nos. 1,326,227 and 2,301,189 a disposable article consisting of an absorbent cellulose foam padding covered on the outer face with a polyethylene sheet and on the inner face with a nonwoven fabric sheet, the assembly being folded along longitudinal lines to form a bellows. The various layers thus formed are welded together in their middle region while the edges can be spread out to pass round the user's waist.

Such a device has, however, the following disadvantage: When it is emitted, the fluid encounters only a single thickness of cellulose foam in the central part, since it cannot pass through the various thicknesses on account of the presence of the impermeable sheet. The same applies at the parts situated in front of and behind the user, since the diaper is spread out when in position.

In order to overcome this disadvantage, U.S. Pat. No. 3,746,592 describes an absorbent padding folded in the shape of a C, having two superimposed layers and a central channel. This device permits an improved distribution of the urine, but has two major drawbacks.

The padding is of substantial constant thickness over its whole surface, which makes it difficult to adapt to the user's anatomy. It is in fact preferable that the regions designed to pass round the top of the thighs, which regions are often provided with elasticated strips, have a degree of flexibility.

Furthermore, the liquid is "stored" in a region which is too close to the user's skin. Admittedly, the liquid is in part drained towards the outer layer, but it also tends to return to the inner layer, which consequently considerably reduces the effect sought.

The invention has the object of overcoming these disadvantages by proposing an absorbent article which has improved absorption while providing for very good adaptation to the user's anatomy.

According to the invention, the absorbent article is characterized in that it incorporates an absorbent padding of substantially rectangular shape, covered on its inner face with a sheet which is permeable to liquids such as a non-woven fabric sheet, and on its outer face a sheet impermeable to fluids such as a polyethylene sheet, these two sheets being partially or totally welded together along their edges, and in that the absorbent padding is formed from at least three superimposed layers consisting of one or more sheets of cellulose foam, the outer layer being continuous while the other layers consist of two juxtaposed half-layers arranged symmetrically with respect to the longitudinal axis of the padding.

In this description, the adjective "inner" denotes the face or layer which is closest to the user's skin, while the adjective "outer" denotes the face or layer furthest removed from the user's skin.

The central channel formed by the juxaposition of the half-layers enables the liquid to drain towards the outer layer, and thus provides for storage of the liquid away from the user's skin, in the outer layer.

It is preferable, both for reasons of manufacture and absorption capacity, that the absorbent padding should be formed from a single layer and incorporates a longitudinal central strip corresponding to the outer layer and at least two lateral strips located on either side of the central strip and folded onto the inner face of the latter in a zigzag (pleated) so as to form the other layers.

For reasons which will be explained below, it is preferable that the padding should consist of an odd number of superimposed layers. Advantageously, this padding will consist of three superimposed layers: this preferred form of the invention enables very good absorption, sufficient distance between the user's skin and the site at which the liquid is stored, and a very good standard of comfort to be obtained together.

It is also desirable that the longitudinal edges of the inner layer, in the case where the absorbent padding incorporates an odd number of layers, should be extended beyond the longitudinal edges of the outer layer, in order to form two lateral single-layer extensions. The presence, in the longitudinal edges, of a single layer permits better adaptation to the user's anatomy. In this case, the padding incorporates a longitudinal central region having several thicknesses and single-layer longitudinal lateral regions.

The advantages listed above are further enhanced by the presence, in the outer layer, of particles of "superabsorbent" at least in the region where the fluid is received. The "superabsorbent" particles are water-insoluble hydrocolloidal polyelectrolytes and absorb several times their weight of aqueous fluid. These compounds are, for example, described in U.S. Pat. No. 4,043,952. Advantageously, the outer layer will be formed from two superimposed sheets and the superabsorbent particles will be inserted between these two sheets.

In order to ensure the optimum migration of the liquid, it is essential that only the outer layer incorporates these superabsorbent particles.

The invention will be better understood by reference to an embodiment of the prior art (U.S. Pat. No. 3,746,592) and four particular embodiments according to the present application. These embodiments are shown in the attached drawings.

Figure 1:
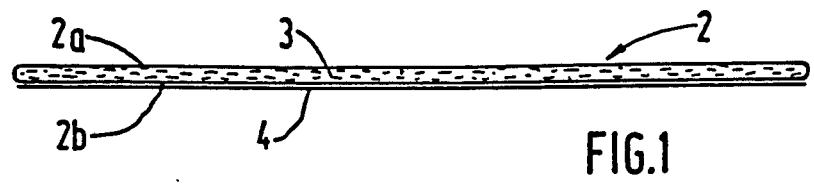
FIG. 1 is a cross-section of a first type of unfolded absorbent padding not incorporating superabsorbent particles.
Figure 2:
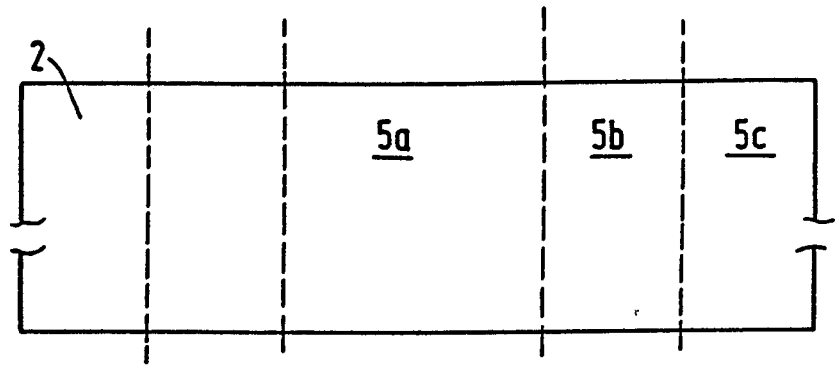
FIG. 2 is a top view of the absorbent padding as illustrated in FIG. 1.
Figure 3:
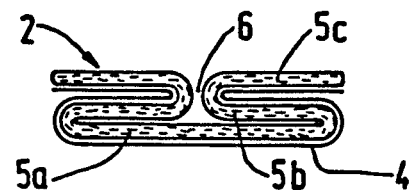
FIG. 3 is a cross-section of the same absorbent padding as that illustrated in FIG. 1, but folded into three superimposed layers.
Figure 4:
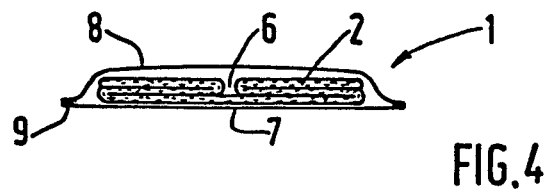
FIG. 4 is a cross-section of an absorbent article incorporating the same absorbent padding as that illustrated in FIG. 3, but compacted.
Figure 5:
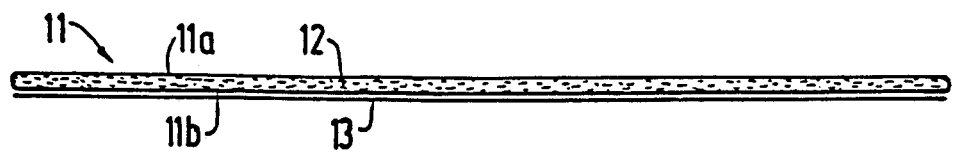
FIG. 5 is a cross-section of a second type of unfolded absorbent padding, not incorporating superabsorbent particles.
Figure 6:
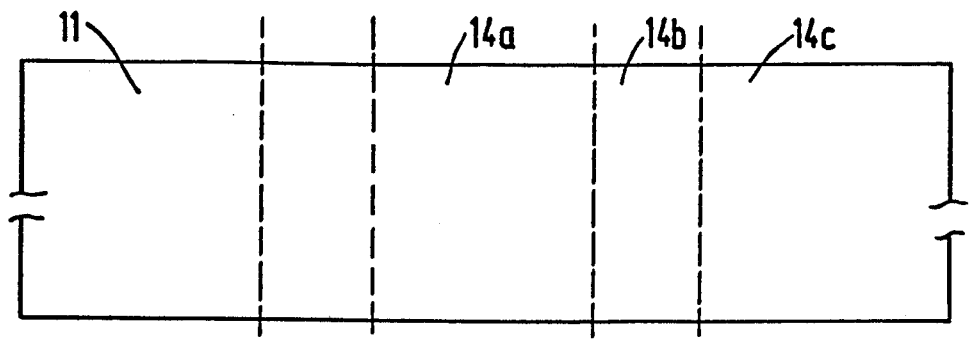
FIG. 6 is a top view of the absorbent padding illustrated in FIG. 5.
Figure 7:
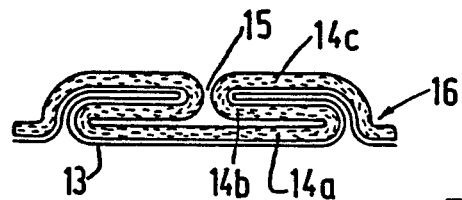
FIG. 7 is a cross-section of the same absorbent padding as that illustrated in FIG. 5, but folded into three superimposed layers, the inner layer being extended by single-layer lateral extensions.
Figure 8:
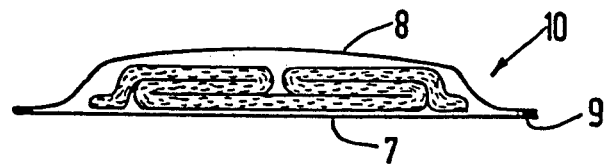
FIG. 8 is a cross-section of an absorbent article incorporating the absorbent padding illustrated in FIG. 7, but compacted.
Figure 9:
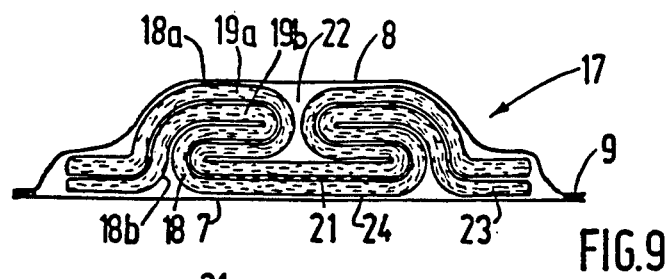

FIG. 9 is a cross-section of a third type of folded absorbent padding, incorporated in the relevant absorbent article. In order to avoid burdening the description needlessly, the absorbent padding has, in contrast to the two previous types of embodiment, not been shown unfolded in cross-section. As a reminder, the reader will be able to refer to FIGS. 5 and 6.

Figure 10:
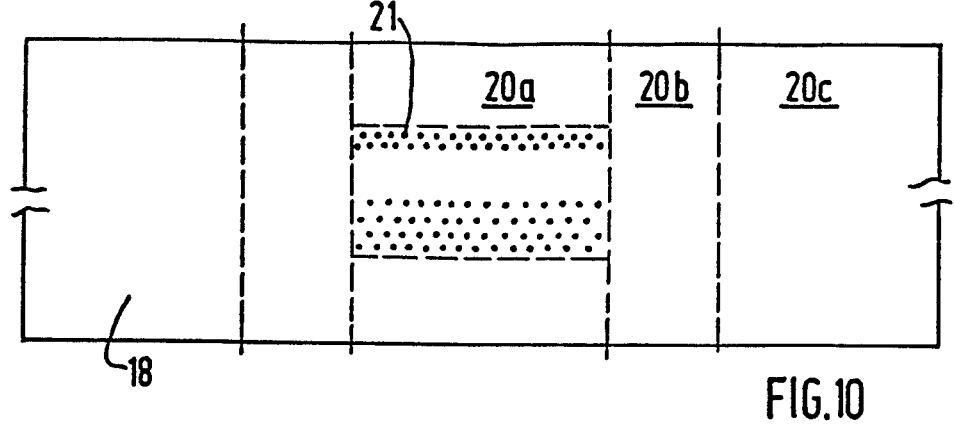

FIG. 10 is a top view of the absorbent padding of FIG. 9.

Figure 11:
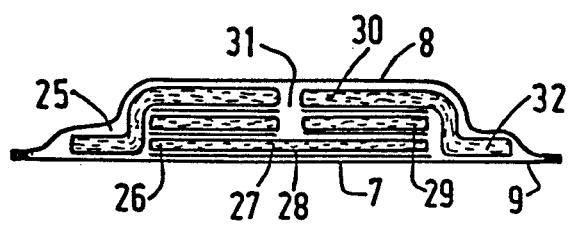

FIG. 11 is a cross-section of a fourth type of noncompacted absorbent padding already incorporated in the relevant absorbent article. The same comment applies as for the absorbent padding illustrated in FIG. 9.

Figure 12:
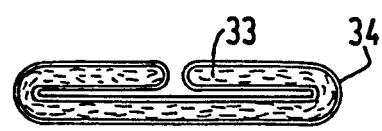

FIG. 12 is a cross-section of an absorbent padding described in U.S. Pat. No. 3,746,592.

According to FIGS. 1, 2, 3, and 4, the article 1 is formed by a rectangular absorbent padding 2 having an inner face 2a and an outer face 2b. The absorbent padding 2 consists of a sheet of cellulose foam 3 supported by a sheet of cellulose padding 4.

The absorbent padding 2 is divided into five longitudinal strips:

A central strip 5a, the outer face of which is designed to form the outer face of the absorbent padding 2 once the latter is folded.

Two intermediate strips 5b on either side of the central strip 5a, equal in width to half the width of the central strip 5a.

Two lateral strips 5c forming the longitudinal ends of the absorbent padding 2, the inner faces of which are designed to form the inner face of this padding. The width of the strips 5c is equal to that of the strips 5b. When the strips 5b and 5c are folded in a zigzag onto the inner face of the strip 5a, a central longitudinal channel 6 is formed.

The folded absorbent padding is then covered on its outer face with a sheet of polyethylene 7 and on its inner face with a sheet of non-woven fabric 8, the two sheets being welded at 9 along the entire length of their edges.

According to FIGS. 5, 6, 7, and 8, the article 10 is formed from a rectangular absorbent padding 11 having an inner face 11a and an outer face 11b. The absorbent padding 11 consists of a sheet of cellulose foam 12 supported by a sheet of cellulose padding 13.

The absorbent padding 11 is divided into five longitudinal strips:

A central strip 14a, the outer face of which is designed to form the outer face of the absorbent padding 11 once the latter is folded.

Two intermediate strips 14b on eithe side of the central strip 14a, equal in width to half the width of the central strip 14a.

Two lateral strips 14c forming the longitudinal ends of the absorbent padding 11, greater in width than strips 14b, the inner faces of which are designed to form the inner face of this padding once the latter is folded. When the strips 14b and 14c are folded in a zigzag onto the inner face of the strip 14a, a longitudinal central channel 15 is formed and also two single-layer longitudinal extensions 16.

The folded absorbent padding is then covered on its outer face with a sheet of polyethylene 7 and on its inner face with a sheet of non-woven fabric 8, the two sheets being welded at 9 along the entire length of their edges.

According to FIGS. 9 and 10, the article 17 is formed by a rectangular absorbent padding 18 having an inner face 18a and an outer face 18b, and consists of two superimposed rectangular cellulose foam sheets 19a and 19b supported by a sheet of cellulose padding 24.

The absorbent padding 18 is divided into five longitudinal strips:

A central strip 20a, the outer face of which is designed to form the outer face of the absorbent padding 18 and in the middle region of which superabsorbent particles 21 are deposited between the two sheets 19a and 19b.

Two intermediate strips 20b situated on either side of the central strip 20a and equal in width to one half the latter.

Two lateral strips 20c forming the ends of the absorbent padding 18, greater in width than strips 20b, and the inner faces of which are designed to form the inner face of this absorbent padding.

When the strips are folded in a zigzag onto the inner face of the strip 20a, a central channel 22 is formed and also two single-layer longitudinal extensions 23.

The folded absorbent padding 18 is then covered on its outer face with a sheet of polyethylene and on its inner face with a sheet of non-woven fabric 8, the two sheets being welded at 9 along the entire length of their edges.

According to FIG. 11, the article is formed by an absorbent padding 25 consisting of an outer layer 26, made up of a sheet of cellulose foam 27 supported by a sheet of cellulose wadding 28, and of two pairs of superimposed half-layers 29 and 30 arranged on the inner face of the outer layer 26 on either side of the longitudinal axis of the latter, each of these half-layers being supported by a sheet of cellulose padding. The juxtaposed half-layers thus form a drainage canal 31. Furthermore, the inner half-layers 30 have extensions 32 which form external longitudinal strips. As above, the absorbent padding is covered with a sheet of non-woven fabric 8 and a sheet of polyethylene 7 welded at 9 along their edges.

By way of comparison, there is illustrated in FIG. 12 a C-shaped absorbent padding formed by a sheet of cellulose foam 33 encased in a sheet of cellulose padding 34.

I claim:

1. Liquid-absorbent disposable article comprising an absorbent pad of substantially rectangular shape and covered on its inner face with a sheet which is permeable to fluids and on its outer face by a sheet impermeable to fluids, said sheets being partially or totally sealed along their edges to form an envelope, said absorbent pad including a continuous outer layer and inwardly positioned therefrom a plurality of juxtaposed half layers defining a narrow channel between said half layers, each of said half layers having a width equal to or substantially equal to one-half the width of said outer layer, the innermost of said half layers extending beyond the longitudinal edges of the outer layer to form two lateral single layer extensions which conform to the sealed edges of said envelope.

2. The disposable article of claim 1 wherein said absorbent pad is formed by a single sheet which includes a longitudinal central strip corresponding to said outer layer and at least two lateral strips on either side of the central strip which are folded in a zigzag onto the inner face of the central strip so as to form the half layers and extending beyond to the longitudinal edges of the outer layer to form said lateral extensions which conform to the sealed edges of said envelope.

3. The disposable article of claim 2 wherein the absorbent pad consists of an odd number of superimposed layers.

4. The disposable article of claim 3 wherein the number of superimposed layers is three.

5. The disposable article of claim 1 wherein said layers are supported by a sheet of cellulose wadding.

6. The disposable article of claim 1 wherein the outer layer only incorporates superabsorbent particles at least in the region in which the fluids are received.

* * * * *